United States Patent [19]

Blum et al.

[11] Patent Number: 5,661,177
[45] Date of Patent: Aug. 26, 1997

[54] ZINC CYSTEATE ITS PREPARATION AND USES IN PHARMACY AND COSMETOLOGY

[75] Inventors: Jean Blum, Courbevoie; Olivier Guillard, Poitiers, both of France

[73] Assignee: Chimie et Biologie, Colombes, France

[21] Appl. No.: 599,419

[22] Filed: Jan. 16, 1996

Related U.S. Application Data

[63] Continuation of Ser. No. 291,403, Aug. 16, 1994, abandoned, which is a continuation-in-part of Ser. No. 980,646, Nov. 24, 1992, abandoned, which is a continuation-in-part of Ser. No. 698,394, May 10, 1991, abandoned, which is a continuation-in-part of Ser. No. 433,569, Nov. 8, 1989, abandoned.

Foreign Application Priority Data

Nov. 9, 1988 [FR] France ................... 88 14909

[51] Int. Cl.$^6$ ................................ A61K 31/315
[52] U.S. Cl. .................. 514/494; 514/864; 556/134; 562/557
[58] Field of Search .................. 424/401, 614, 424/641, 642, 643; 514/494, 864; 562/557; 556/134

[56] References Cited

U.S. PATENT DOCUMENTS

| | | | |
|---|---|---|---|
| 4,053,630 | 10/1977 | Yu | 424/289 |
| 4,154,815 | 5/1979 | Pader | 424/50 |
| 4,224,339 | 9/1980 | Van Scott | 424/289 |
| 4,259,508 | 3/1981 | Blum | 549/72 |
| 4,618,625 | 10/1986 | Vinas | 514/494 |
| 4,711,780 | 12/1987 | Fahim | 424/145 |

FOREIGN PATENT DOCUMENTS

| | | |
|---|---|---|
| 0 062 362 | 10/1982 | European Pat. Off. . |
| 2 241 301 | 3/1975 | France . |
| 991552 | 5/1965 | United Kingdom . |

*Primary Examiner*—Gollamudi S. Kishore
*Attorney, Agent, or Firm*—Horst M. Kasper

[57] ABSTRACT

A process of treatment against seborrhea and/or for the cicatrization of wounds and/or for stimulation of skin cell growth involving a topical application and/or an oral administration of any composition that contains zinc cysteate, wherein zinc cysteate is based on the following formula $$-O-SO_2-CH_2-CH(NH_2)-CO-O-ZN-$$

and wherein the zinc cysteate is in an anhydrous or a hydrated form. Zinc cysteate is dehydrated and based on the formula $$C_3H_5O_5NSZSa, 2H_2O.$$

5 Claims, No Drawings

ZINC CYSTEATE ITS PREPARATION AND USES IN PHARMACY AND COSMETOLOGY

CROSS-REFERENCE TO RELATED APPLICATIONS

This is a file wrapper continuation application of application Ser. No. 08/291,403, filed Aug. 16, 1994, now abandoned, which is a continuation-in-part application of another application filed Nov. 24, 1992 and bearing Ser. No. 07/980,646, now abandoned, which is a continuation-in-part of another application filed May 10, 1991 and bearing Ser. No. 07/698,394, now abandoned, which is a continuation-in-part application of another application filed Nov. 8, 1989 and bearing Ser. No. 07/433,569, now abandoned. The entire disclosure of this latter application, including the drawings thereof, is hereby incorporated in this application as if fully set forth herein.

BACKGROUND OF THE INVENTION

1. Field of the Invention

The present invention relates to a method of production of a zinc cysteate, its preparation and uses in pharmacy and cosmetology.

2. Brief Description of the Background of the Invention Including Prior Art

Mixtures containing various constituents, where possibly various metals, susceptible to chelate the cysteic acid, are added to the cysteic acid, are taught in the U.S. Patent No. 4,224,339 to Van Scott et al. In this reference a salt is a composition comprising a negative anion and a positive cation which are bonded to each-other by a heteropolar bond and where this heteropolar bond disappears during the dissolution, for example in water, and creates thus two ions, the anion and the cation, which is, in this case, the cysteic acid ion and the zinc cation. A chelate on the other hand is a chemical entity, wherein a metal is bonded to another molecule or ion, which is in general organic, by a covalent bonding process or by coordination based on free electron pairs of the one and the holes of the second atom.

The invention zinc cysteate is a salt composed of two ions which are bonded by heteropolar forces. In contrast, the U.S. Pat. No. 4,224,339 requires the presence of chelates, where the metals are bonded to the remainder of the molecule by covalent forces or coordination forces.

The existence of zinc was recognized in biology more than a century ago and the book of Jean Lederer "Le zinc en Pathologie et en Biologie" (Zinc in Pathology and Biology) published by Nauwelaerts in Brussels (1985) is an abstract of up-to-date knowledge about the subject.

Olivier Guillard teaches in his thesis "Metabolism of a New Zinc Pantothenate" for the Degree of Doctor of Pharmacy, Poitiers University, 1978, that the zinc salt of 2-pyridine-thione is used in many hair lotions against dandruff.

Zinc is essential for growth and multiplication of cells and a deficiency in zinc impairs the cicatrization of wounds. However, A. Favier at al. teach in the publication Lyon Pharmaceutiques, 1980, 31, 6, pp. 357–366, that in a normal animal, i.e. without zinc deficiency, extra zinc does not accelerate the cicatrization.

Then it is quite surprising that the new salt of the present invention, zinc cysteate, has peculiar cicatrizing qualities, all the more because the organic anion of the salt, cysteic acid, is unknown for this therapeutic use, moreover because its sulfur function is in an oxidized form.

As a matter of fact, scientific literature learns that it is in the reduced form of mercaptan that sulfur compounds, for instance glutathione, are cicatrizing agents.

It is known in the art that zinc cysteate and cysteic acid are two different compositions and that each of these two compositions can crystallize in water with a number of associated molecules of water of hydration.

If a hydride is heated, it will lose its water above a critical temperature. A person of ordinary skill in the art knows that the dihydrate obtained by concentration of an aqueous solution or by recrystallization in water can be separated and dried at 30° to 40° C. Such a mild drying temperature is used because at a higher temperature the two water molecules of crystallization start to evaporate and this occurs at ordinary pressure. The anhydrous salt is obtained by heating to 105° C. at ambient pressure. The organic salts generally lose their crystallization water before this temperature is attained. This is used to a very large extent in pharmaceutical preparations for evaluation of the loss occurring during drying based on which one measures in particular the number of the water molecules in the hydrated crystals. Therefore, a drying has to take place at 105° C. in order to obtain an anhydrous product.

The hydration of CB 619 in salt form, where CB 619 is the code name of the dihydrated zinc cysteate, occurs in that the number of associated water molecules is calculated by the weight difference between the hydrated product, dried at a temperature of 30° to 40° C. as indicated, and the same product dried to a constant weight at a higher temperature, in particular at a temperature of 105° C. as indicated above.

For example, if the weights Pa and Pb before and after drying, and if M is the molecular weight of the anhydrous salt, the number N of the water, molecules associated to each salt molecule is furnished by the following formula:

$$N = M(Pa - Pb)/18\ Pb.$$

SUMMARY OF THE INVENTION

1. Purpose of the Invention

It is an object of the present invention to provide for a zinc cysteate with pharmaceutical properties.

It is a further object of the present invention to provide for a zinc cysteate with cosmetological properties.

It is another object of the present invention to provide for a zinc cysteate with antifungic properties.

The novel features which are considered as characteristic for the invention are set forth in the appended claims. The invention itself, however, both as to its method of operation, its products and physical requirements, together with additional objects and advantages thereof, will be best understood from the following description of specific embodiments and examples.

DESCRIPTION OF INVENTION AND PREFERRED EMBODIMENT

The present invention relates to anhydrous or hydrated cysteate of zinc according to the formula:

The present invention relates particularly to a dihydrate of the zinc salt of L-cysteic acid according to the formula:

which will be hereinafter designated by the code name CB 619.

CB 619, a white crystalline powder with an astringent taste, is to be sheltered from light in a stoppered container. CB 619 is insoluble in usual organic solvents, but soluble in dimethyl sulfoxide. In water, its solubility is close to 6 weight-percent by volume. The pH of a 6% solution is about 6.30.

In a 0.1% solution in 0.1N hydrochloric acid, its U.V. spectrum has broad bands at 3,500 and 3,400 $cm^{-1}$, and the band of C=O group at 1,600 and 1,200 $cm^{-1}$ —O—$SO_2$ group at 1,400 and 1,100 $cm^{-1}$ S=O group at 900 $cm^{-1}$ It has been found that CB 619, zinc cysteate according to the present invention, has also unforeseeable antifungic properties. CB 619 was tested against Pityrosporum orbiculare 1219 and Pityrosporum ovale 1363, both from the Pasteur Institute, in the Dixon's culture medium, modified by Randjandiche according to the following composition:

| | |
|---|---|
| Malt extract agar (from oxoid) | 60 g |
| Ox bile (from oxoid) | 20 g |
| Tween 40 | 10 ml |
| Distilled water | 1,000 ml |

30 ml of culture medium were cast in each Petri dish of 90 mm of diameter.

The inoculum was a 2 ml suspension of Pityrosporum containing 10,000,000 germs, 72 hours old, per ml.

After drying at 37° C., tests were carried out according to discs method or to cylinders method.

According to cylinders method, cylinders of 4 mm of diameter were excavated in gelose with a stainless steel tool, and 75 microliters of the solution of the tested product were introduced into each cylinder.

According to the discs method, discs of 6 mm of Antibiotica-Testblättchen Schleider & Schull, reference 2668/2, are soaked in test solution, then set down onto the seeded medium.

According to both methods, the inhibition areas were measured after a time of incubation of 72 hours at 37° C.

According to cylinders method, Intrinsic Inhibition Power of CB 619 is, the inhibition diameter being given in mm:

| | Pityrosporum ovale | Pityrosporum orbiculare |
|---|---|---|
| concentration of 0% | 4 | 4 |
| concentration of 2% | 10 | 10 |
| saturated solution | 11 | 11 |

According to the discs method, Intrinsic Inhibition Power of CB 619 is, the inhibition diameter being given in mm:

| | Pityrosporum ovale | Pityrosporum orbiculare |
|---|---|---|
| distilled water | 4 | 6 |
| 1 mg CB 619 | 6 | 6 |
| 2 mg CB 619 | 7 | 7 |
| 3 mg CB 619 | 9 | 9 |
| 4 mg CB 619 | 11 | 11 |
| 5 mg CB 619 | 13 | 13 |

Then, CB 619 may be used in the therapy of fungic deseases, particularly of skin fungic deseases. For local use preparations, zinc cysteate is preferably at a concentration of 1 to 5%, and the ointment containing 3% of CB 619 admixed to 59 g of polyethylene glycol, 37 g of polypropylene glycol, 1 g of polysorbate, and 3 g of distilled water, is a non limitative example useful as an antifungic drug for the skin.

According to the invention, zinc cysteate in any hydrated form, even in the anhydrous form, is endowed with the above cited antifungic properties. Only the concentration of active principle will vary according to its water content.

The interesting antifungic properties of zinc cysteate may be used for human beings or animals.

The present invention relates also to the manufacturing process of the cysteate of zinc comprising reacting cysteic acid with salt, oxide or hydroxide of zinc, preferably in water, because it is an inexpensive solvent. According to the invention, it is possible to use a salt, preferably soluble in water, of cysteic acid instead of cysteic acid itself.

According to another process of the invention, cysteate of zinc is obtained by the action of zinc peroxide onto cystine or cysteine in a slightly acidic solution, for instance, when using cystine or cysteine hydrochlorides.

However, the last process leads to a less pure cysteate of zinc and in order to obtain a salt of pharmaceutical grade, it must be purified for instance by several recrystallizations.

The new manufacturing processes of zinc cysteate according to the invention will be better understood when reading the following examples which are non-limitative and may have many different forms within the scope of the invention.

EXAMPLE 1

Manufacturing from zinc sulfate 3.744 g of L-cysteic acid monohydrate are dissolved in 55.94 ml of a barium hydroxide solution 0.715N.

On the other hand, 3.558 g of zinc sulfate monohydrate are dissolved in 50 ml of distilled water.

Both solutions are mixed which leads to a precipitation of barium sulfate which is filtered off and washed twice with 10 ml of water. Filtrates are brought together and evaporated in vacuo. Crude CB 619 is then obtained and is recrystallized in twice its weight of water, washed with 5 ml of methanol, then dried in an oven at a temperature of 30°–40° C.

EXAMPLE 2

Manufacturing from zinc oxide 16.92 g of anhydrous L-cysteic acid are dissolved in 200 ml of distilled water and 8.14 g of zinc oxide are added. The mixture is heated to a boiling point, the oxide being almost completely dissolved. After having added some discoloring carbon black, the solution is filtered. The filtrate is evaporated in vacuo until its volume is reduced to about 100 ml. This is cooled and CB 619 crystallizes. It is filtered off, washed twice with 20 ml portions of methanol and dried in an oven at a temperature of 30°–40° C.

EXAMPLE 3

Manufacturing from zinc carbonate 550 g of anhydrous L-cysteic acid are partly dissolved in two liters of distilled water and 510 g of powdered zinc carbonate are added while stirring. The stirred mixture is heated to a boiling point, and when an almost limpid solution is obtained, some discoloring carbon black is added. The hot mixture is filtered and the filtrate is cooled to a temperature of 0°–5° C. Crystals of crude CB 619, precipitating from the solution, are filtered off and the product is recrystallized as previously in twice its weight of water, washed with two portions of methanol, and dried in an oven at a temperature of 30°–40° C.

EXAMPLE 4

Manufacturing from zinc peroxide and cysteine hydrochloride 17.55 g of cysteine hydrochloride monohydrate are dissolved in 250 ml of water and, 70 g of zinc peroxide are added accompanied by stirring. A thick mixture is obtained and it is stirred at a temperature of 30°–35° C. for four hours. Residual solid particles are filtered off and washed with two portions of 50 ml of water. The filtrates are brought together and evaporated in vacuo until the volume is reduced to 60 ml. When cooling to a temperature of 0°–5° C. crude CB 619 precipitates. It must be recrystallized at least twice over to obtain a product as pure as in examples 1, 2, and 3. It is washed with methanol and dried as specified above.

The present invention also relates to the pharmaceutical use, and particularly to the dermatological use of zinc cysteate when it is alone or associated with other drugs.

The useful pharmaceutical properties of zinc cysteate were disclosed in several experiments the datas of which are being summarized in the following.

Acute toxicity of CB 619 in the Mouse

The lethal dosis 50% (LD 50) of CB 619 were evaluated when dissolved in bidistilled water and administered by 0.2 to 0.3 ml/kg volumes, monitoring the effect during 14 days.

According to the Miller and Tainter method, the LD 50 for male and female animals were calculated at 0.10±0.013 g/kg when the drug was given intraperitoneally, and 1.65±0.06 g/kg when given orally.

At the toxic dosis, animals become isolated in their cage. Their hair stands up and they move with difficulty. No diarrhea was observed.

Skin irritation index of CB 619 in the Rabbit

The experiment was made according to the French "Arrete Ministeriel" of the 21th of February 1982 which specifies the official method for the determination Of the skin primary irritation index (SPI).

The skin primary irritation was found at 0.1666, number much under 0.5 which is the number above which a product is classified lightly irritant.

CB 619 is then non-irritant.

The official method for the determination of the index of primary cutaneous irritation is described in detail in Annex 1.

Eye tolerance of CB 619 in the Rabbit

The experiment was made according to the recommendations of the French "Arrete Ministeriel" of the 21 February 1984 which specifies the official method to determinate the eye irritation (E.I.). This official method is described in detail in annex 2.

In first approximation the maximum eye irritation of CB 619 is 5.83 and is then very weakly irritant. The conclusion is confirmed by the fact that after 48 hours, the eye-irritation is under 2.

Allergenicity degree of CB 619 according to the sensibilization in the Guinea Pig:

The experiment was made according to the technical sheet No. 44 (J. Pharmacol. Paris, 1978, 9, 1, 103–6) which conforms to the Magnusson and Kligmann technique.

In the absence of specific reaction of the skin of Guinea Pig, one may come to the conclusion that CB 619 has no allergenic properties according to the sensibilization test of Magnusson and Kligmann. This sensibilization test according to Magnusson and Kligmann is described in detail in annex 3.

In vitro antiseborrheic properties of CB 619

According to the experiment, the lipidic metabolic activity of the prepucial gland of the rat was evaluated. The lipidic synthesis of the sebaceous gland was evaluated by adding, as marked precursor, sodium $^{14}$C-acetate.

CB 619 was tested in comparison with carboxymethylcysteine (CMC) as a reference.

CMC at $10^{-4}$M leads to an inhibition of 5.9%
CB 619 at $10^{-4}$M leads to an inhibition of 33.7%
CMC at $10^{-3}$M leads to an inhibition of 24.5%
CB 619 at $10^{-3}$ leads to an inhibition of 41.8%
CB 619 at $10^{-2}$M leads to an inhibition of 51.5%
CMC is not enough soluble at $10^{-2}$M to test it at this concentration.

In short, at the concentration of $10^{-2}$M, CB 619 gives an average inhibition of the lipidic synthesis which is above 50% and, at the concentration of $10^{-3}$M, both molecules are active, CB 619 being the more active.

Cicatrizing activity of CB 619 in the rat

The experiment was to calculate the area of the wound made by loss of substance.

When spread onto a wound in a 2% carbopol gel, CB 619 enhances cicatrization at the concentration of 3%, but is no more active at 10%.

Cytoxicity of CB 619 for human fibroblast cells

Two lots of human fibroblast cells of the same strain were tested;. first log as standard and second lot in contact with a solution of CB 619 at a determined concentration. The tested concentrations were 50,5 and 1 microgram/ml.

At 50 microgram/ml, CB 619 reduces the cell growth: that may be noticed after 48 hours. Afterwards, cells die.

At 1 and 5 microgram/ml, the product increases the 5 cell multiplication in accordance with the concentration.

The increase is significant on the sixth day when concentration is 1 microgram/ml, and on the fourth, sixth and eighth days, when the concentration is 5 microgram/ml.

Because of the interesting properties of zinc cysteate, the present invention relates also to its cosmetological applications and uses.

The present invention relates also to pharmaceutical and cosmetological preparations that contain zinc cysteate.

For local use preparations, the zinc cysteate is preferably at a concentration of 1 to 5%. A non-limitative example is a cicatrizing and antiseborrheic ointment made by adding CB 619 at the concentration of 3% in a mixture of 59 g of polyoxyethylene glycol, 37 g of polypropylene glycol, 1 g of polysorbate, and 3 g of water of La Roche-Posay.

It will be understood that each of the elements described above, or two or more together, may also find a useful application in other types of zinc cysteate, its preparation and uses in pharmacy and cosmetology differing from the types described above.

While the invention has been illustrated and described as embodied in the context of a zinc cysteate, its preparation and uses in pharmacy and cosmetology, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

ANNEX I

OFFICIAL METHOD FOR THE DETERMINATION OF THE INDEX OF PRIMARY CUTANEOUS IRRITATION

I. PURPOSE

The present method is utilized so as to determine the index of primary cutaneous irritation for a cosmetic or bodily hygiene product.

II. Field of application

This method applies only to products which do not indelibly color the skin.

III. Principle

This method is based on the observation of cutaneous reactions provoked through the sole application of the principle.

IV. Experiment animals and equipment 4.1. Male albino rabbits of defined breed, weighing around 2.5 kg. So as to be perfectly acclimated, the animals must be kept in individual cages for one week prior to the experiment, and; must receive food of invariably balanced composition.

4.2. Maintenance apparatus allowing for satisfactory realization of the experimental protocol.

4.3. Electric shears for animal, equipped with a card (height of section: 0.05 mm).

4.4. Sterile vaccinostylets.

4.5 Pieces of pharmacopeial absorbent cotton of three layers with a surface of 6.2 cm², either square at 2.5 cm per side, or round with diameter of 2.8 cm; one side is covered with hypoallergenic and impermeable adhesive film or any equivalent system, for example a pliable and inert capsule preventing the diffusion of highly fluid liquids outside the bandage dressing.

4.6. Microporous hypoallergenic adhesive bandage of a width of 50 mm, or any equivalent non-occlusive system.

4.7. Protection compress in Codex absorbent cotton of suitable dimensions.

4.8. Pliable and aerated maintenance apparatus for the dressings, bandaged or in sparadrap.

4.9. Sterile syringe, 1 ml per tenth.

4.10. Laboratory scale sensitive to at least a milligram.

V. Operating procedures 5.1. Preparation of the skin:

5.1.1. The day before application of the product, shear the back and flanks of the rabbits (4.1) with shears (4.3) so as to clear a surface of about 14 cm×14 cm; proceed with care in order to avoid all irritation. Verify skin condition so as to retain but six animals presenting healthy and clean-shaved skin.

5.1.2. To the right of the spinal column, with the use of a vaccinostylet, effectuate three parallel scarifications along a length of about 2.5 cm, with about 0.5 cm between each one. The scarifications of the epidermis must not reach the dermis; they are brought about without bleeding.

5.2. Application of the product:

5.2.1. Apply the product to the scarified and non-scarified zones of the skin either directly, or else after having deposited it on the gauze material so as to avoid all loss.

Required quantities:

| Liquid products | 0.5 ml |
|---|---|
| Semi-liquid and pasty products | 0.5 ml or 0.5 g |
| Solid and pulverulent products | 0.5 g |

5.2.1.1. The liquid products are deposited by use of the syringe (4.9) onto two pieces of gauze (4.5) which are immediately applied to the skin (5.2.1).

5.2.1.2. The semi-liquid and pasty products are applied directly onto the skin (5.2.1) and then covered with the pieces of gauze (4.5).

5.2.1.3. The solid and pulverulent products are applied onto the skin (5.2.1) and then covered by the pieces of gauze (4.5) which have been humidified beforehand with 0.5 ml of distilled water, or water of equivalent quality.

5.2.2. Maintain in contact with the skin, both the product and the piece of gauze; do this on each of the two zones by means of the adhesive bandage (4.6).

5.2.3. Put the protection compress (4.7) in place.

5.2.4. Maintain everything in place by means of the dressing apparatus (4.8); this will be specified in the report on the experiment.

5.2.5. Remove the dressing and the pieces of gauze 24 hours following application of the product.

Evaluation of the primary cutaneous irritation:

Primary cutaneous irritation must be evaluated around thirty minutes subsequent to removal of the dressing; a second evaluation is to take place 48 hours later, i.e. 72 hours after application of the product. Observations are effected on the two zones, scarified and non-scarified, in accordance with the following numerical scale.

5.3.1. Erythema and scab formation

| No erythema | 0 |
|---|---|
| Light erythema, i.e. hardly visible | 1 |
| Highly visible erythema | 2 |
| Quite sizable erythema | 3 |
| Serious erythema, i.e. crimson red with or without scabs, deep-seated lesions | 4 |

5.3.2. Oedema formation

| No oedema | 0 |
|---|---|
| Very light oedema, i.e. hardly visible | 1 |
| Light oedema, i.e. well-defined contours, evident swelling | 2 |
| Medium oedema, i.e. about 1 mm thick | 3 |
| Serious oedema, i.e. thickness superior to 1 mm and surface greater than that of the application zone | 4 |

VI. Determination of the index of primary irritation 6.1. Add the figures gathered concerning erythema and oedema after 24 and after 72 hours on both the six non-scarified and the six scarified zones.

6.2. Add the thereby obtained figures and calculate the average value by dividing the sum total by 24.

This average value is to be taken to represent the index of primary cutaneous irritation (PCI).

7. Expression of the results

| Non-irritating | $PCI \leq 0.5$ |
|---|---|
| Slightly irritating | $0.5 < PCI \leq 2$ |
| Irritating | $2 < PCI \leq 5$ |
| Highly irritating | $5 < PCI \leq 8$ |

Animals who die in the course of the experiment are to be replaced by other animals who will be treated under the same conditions.

ANNEX II
OCULAR IRRITATION

I. Purpose

The present method is utilized so as to evaluate the kind and degree of irritation brought about in the eyes by the use of a cosmetic or bodily hygiene product.

II. Principle

The method is based on observation of ocular reaction provoked by the sole instillation of the product.

III. Experiment animals and equipment

Male albino rabbits of defined breed, weighing around 2.5 kg.

3.1. So as to be perfectly acclimated, the animals must be kept in individual cages for at least one week prior to the experiment, and must also, from their arrival onwards, receive food of invariably balanced composition.

3.2. Maintenance apparatus allowing for satisfactory realization of the experimental protocol.

3.3. Sterile syringe of 1 ml graduated to the hundredth.

3.4. Aqueous solution of sodic fluorescein at 2 p. 100 m/v, preferably prepared extemporaneously.

3.5. Solution of sodium chloride at 9 p. 1000 m/v, or isotonic as regards tears, or an equivalent solution.

3.6. Torch lamp.

3.7. Ophthalmoscope.

3.8. Ultraviolet magnifying lamp of the type utilized in ophthamology.

3.9. Laboratory scale sensitive to at least a milligram

IV. Operating procedures

This test is to be effected on six rabbits possessing healthy eyes with no defect.

Directly apply the product in the conjunctival pouch of one of the eyes in the following doses:
Liquid products: 0.1 ml;
Semi-liquid or pasty products: 0.1 ml or 100 mg;
Solid and pulverulent products: 100 mg.

Maintain the eyes closed for no less than 10 seconds so as to avoid any and all loss.

Maintain the animals for one hour inside the apparatus (3.2) so that they are unable to rub their eyes, then put them back in their cages.

Observe the eye of the rabbits one hour, and then 1, 2, 3, 4 and 7 days following the instillation, utilizing the non-instilled eye as a control in order to evaluate possible irritation in the treated eye.

Tests are to be effected in the following order:
conjunctiva, i.e. chemosis, watering of the eyes, reddening;
iris;
cornea, i.e. degree and surface of opacity.

Observation of lesions of the conjunctiva, the iris, and the cornea is effected by means of direct testing. The observation of the cornea is to be completed by a test following installation of the fluorescein solution (3.4) and rinsing with the sodium chloride solution (3.5); further examinations can be effected with the ultraviolet lamp (3.8).

V. Guidelines

Proceed through the different steps of evaluation of the lesions in the order of instillation of the animals.

Note observations in accordance with the numerical evaluation scale detailed below.

VI. Numerical evaluation of ocular lesions 6.1. Conjunctiva

Begin the evaluation of chemosis and watering before opening the eyelids of the animal.

6.1.1. Chemosis (A):

| | |
|---|---|
| No swelling | 0 |
| Light swelling, including the nictitating membrane | 1 |
| Swelling with eyelid eversion | 2 |
| Swelling with half-closed eyelids | 3 |
| Swelling with eyelids more than half or completely closed | 4 |

6.1.2. Watering (B)

| | |
|---|---|
| Absence of watering | 0 |
| Light watering, light secretions normally occurring in the internal angle are not to be taken into account | 1 |
| Watering, with humidifying of the eyelids and neighboring hairs | 2 |
| Watering with humidifying of the eyelids and hairs on large surfaces around the eye | 3 |

6.1.3. Reddening of the palpebral conjunctiva (C):

| | |
|---|---|
| Normal vessels | 0 |
| Vessels clearly more bloodshot than normally | 1 |
| Vessels difficult to individually distinguish: | |
| Sharp red color, diffuse | 2 |
| Dark red color, diffuse | 3 |

6.1.4. Add the three scores and multiply the total by 2:

$$(A+B+C)\times 2$$

Maximum=20.

6.2 Iris (D):

| | |
|---|---|
| Normal | 0 |
| Clearly more creased than normal, congestion, swelling; iris still reacting to light, even if slowly, one or more of these features | 1 |
| No reaction to light, haemorrhage, considerable destruction, one or more of these features | 2 |

6.3 Cornea

As regards opacification, only the zone presenting the highest degree of lesion is to be taken into account. Zones of corneal attack are distinguished by highly marked fluorescence.

6.3.1. Degree of opacification (E):

| | |
|---|---|
| No visible modification nor loss of glossiness or loss of hair | 0 |
| Presence of diffused or disseminated translucid zones, details of the iris clearly visible | 1 |
| Presence of an easily identifiable translucid zone, details of the iris slightly masked | 2 |
| Presence of an opalescent zone, no detail of the iris visible, contour of the pupil scarcely discernible | 3 |
| Presence of total corneal opacity rendering the iris and the pupil invisible | 4 |

6.3.2. Opaque area (F)

| | |
|---|---|
| A quarter, or less but not negligible | 1 |
| Between a quarter and a half | 2 |
| Between a half and three quarters | 3 |
| From three quarters to the entire surface | 4 |

6.3.3. Multiply these two scores and then multiply the result by 5: (E×F×5),

Maximum=80.

VII. Determination of the indexes of ocular irritation 7.1. Add up the scores gathered for each of the six rabbits as of each time of observation. One thereby obtains the index of individual ocular irritation: I.O.I.

7.2. At each time of observation calculate the average individual ocular irriatation for the six rabbits. One thereby obtains the index of mean ocular irritation: O.I.

7.3. Note among the six ocular irritation scores the one with the highest value. One thereby obtains the index of maximum ocular irritation: M.O.I. The time it takes for the latter to appear will be specified in the minutes or report of the experiment.

VIII. Expression of the results

The appreciation of the examined product will be based upon the different indexes mentioned in point VII, in accordance with the following table.

| VALUES OF THE DIFFERENT INDEXES | | | |
|---|---|---|---|
| M.O.I. | O.I. | I.O.I. | APPRECIATIONS |
| 0–5 | At 1 day = 0 | | Non-irritating |
| >5–15 | At 2 days < 2 | | Hardly irritating at all |
| >15–25 | At 4 days < 2 | | Slightly irritating |
| >25–50 | At 7 days < 20 | <30 for 6 rabbits and <15 for at least 4 at 7 days | Irritating |
| >50–80 | At 7 days < 40 | <60 for 6 rabbits and <30 for at least 4 at 7 days | Very irritating |
| 80 | | | Extremely irritating |

In an initial approximation, the product is classified in one of the six categories in accordance with the maximum ocular irritation scores.

In a second evaluation, the persistence of lesions intervenes as a corrective of the preceding classification; the ocular irritation and individual ocular irritation scores at different times are taken into account:

either by confirming the appreciation of the initial approximation if all attendant conditions are fulfilled;

or else by reclassifying the product in the immediately higher category if all conditions are not fulfilled.

Animals who die in the course of the experiment are to be replaced by other animals who will be treated under the same conditions.

ANNEX III
SENSITIZATION TEST ON GUINEA PIGS.
MAGNUSSON AND KLIGMANN MAXIMIZATION TEST

Principle

This test is designed to create a delayed allergic reaction in the guinea pig.

In principle the method is applied with products in a pure state. Yet in certain cases, especially as regards some injectable solutions or in preparations for external use, one may directly utilize the form of administration.

The following items are generally required in the example:

Female albino Hartley-breed guinea pigs weighing between 300 and 500 grams.

Pharmacopeia vaseline.

Complete Freund adjuvant (DIFCQ Laboratories).

Lauryl sodium sulfate solution (10%) in the vaseline.

A 1 ml syringe.

Short-bevelled needle for intradermic injection B-D YALE 26G 3/8.

Pads of gauze or Whatmann filter paper, 2×4 cm and 2×2 cm.

Plastic adhesive tape, Sparasylval Hypoallergic type, Laboratoires FOURNIER, 9, rue Petitot, Dijon, France.

Electric shears.

Razor.

The example is performed as follows.

1. Determination of the non-irritating concentration to be utilized.

In particular, during the third stage, it is necessary to utilize the product under study in concentrations which are not irritating for the external intradermic and cutaneous tracts.

For the intradermic tract, the product is placed in solution or suspension in bidistilled water, or a suitable solvent. Intradermic injections of 0.1 ml are given in the preliminarily sheared and shaved dorsal region of four albino guinea pigs in increased concentrations. If the preparation under study exists in a commercialized form which can thereby be utilized, the preparation itself, for instance, and its dilutions at ¼, ½, and ¾, are chosen. If the usual solution is unknown, or if the commercialized form is not directly utilizable via the intradermic tract, then, for instance, 0.1, 2, 5, and 10% arbitrary solutions are employed. The reading of possible reactions takes place after 24 hours. If the commercialized preparation, or the usual concentration is not irritating, it will be used for the following tests. If this is not the case, the scale utilized will depend on the maximum non-irritating concentration (MNIC), whose determination may require a second series of tests with concentrations to be determined in accordance with the results of the first.

The same procedures are used for the external cutaneous tract, with the product being placed, in certain cases, in suspension or solution in vaseline. Applications at 0.2 g onto 2×2 cm gauze squares of each concentration are maintained under an occlusive pad by means of an adhesive bandage. Readings are taken one hour following removal of the pads.

2. Sensitization

A series of 20 animals is used.

The dorsal region of each animal is first sheared, then shaved.

On both sides of the spinal column, at the level of the scapula, in a 2×4 cm zone, the following intradermic injections, 0.05 ml each, are given with two injections per solution, one per side:

50% Freund adjuvant in a physiological serum.

Allergen at its usual concentration or at the maximum non-irritating concentration in solution in a suitable solvent.

Mixed solution of 50% Freund adjuvant and allergen at the preceding concentration.

Following an eight-day rest, the injection zone is acted upon as follows:

Painting application with a 10% lauryl sodium sulfate solution in vaseline so as to provoke local cutaneous irritation. 24 hours after the painting, occlusive application with a pad of gauze or a 2×4 cm filter paper covered by the allergen in suspension or solution at its usual concentration or at the maximum non-irritating concentration in vaseline.

The pad is maintained on the animal's back for 48 hours by means of an adhesive bandage of a sparasylval hypoallergic type. After 48 hours, the adhesive bandage is removed.

3. Activation

Fourteen days after the end of the sensitization period, the animal is meticulously sheared and shaved on a flank in an intact area which has been spared contact with the allergen and the adhesive bandage.

A few hours after this operation, an occulsive application of the allergen in suspension or solution in vaseline at its usual or at the maximum non-irritating concentration concentration is effected, where it remains in place for 24 hours.

Readings of local reactions take place 24 and 48 hours following removal of the pad.

The results for each animal can be noted in accordance with skin reactions; a specific reactivity to the allergen may thereby be determined.

| | |
|---|---|
| No reaction | 0 |
| Scattered light blotches | 1 |
| Diffuse, moderate blotches | 2 |
| Intense, puffy blotches | 3 |

4. Determination of the degree of allergenicity

The determination of the degree of allergenicity of the studied substance is usually based on the number of animals in the series having presented a reaction; it is not based on the intensity of the latter.

This five-degree classification is effected in accordance with the following scale:

| Percentage of animals having presented a reaction | Degree of allergenicity |
|---|---|
| 0–8 | I |
| 9–28 | II |
| 29–64 | III |
| 65–80 | IV |
| 81–100 | V |

TABLE I

MAGNUSSON and KLIGMANN maximization method

| | | Note | | | | | |
|---|---|---|---|---|---|---|---|
| Product | Reading | 0 | 1 | 2 | 3 | % | Class. |
| Benzocaine: | | | | | | | |
| Injections 5 p. 100 (alcohol 70%) | 24 | 17 | 3 | 0 | 0 | 15 | II |

TABLE I-continued

MAGNUSSON and KLIGMANN maximization method

| | | Note | | | | | |
|---|---|---|---|---|---|---|---|
| Product | Reading | 0 | 1 | 2 | 3 | % | Class. |
| Application 10 p. 100 Activation 2.5 p. 100 Diamine paraphenylene: | 48 | 17 | 3 | 0 | 0 | 15 | II |
| Injection 0.05 p. 100 (serum) | 24 | 3 | 13 | 4 | 0 | 85 | V |
| Application 1 p. 100 Activation 0.05 p. 100 Procainamide: | 48 | 4 | 12 | 4 | 0 | 80 | IV |
| Injection 10 p. 100 (injectable commercialized solution) | 24 | 6 | 5 | 9 | 0 | 70 | IV |
| Application 10 p. 100 Activation 10 p. 100 Thioglycerol: | 48 | 6 | 5 | 9 | 0 | 70 | IV |
| Injection 5 p. 100 (serum) | 24 | 7 | 9 | 3 | 0 | 63 | III |
| Application 10 p. 100 Activation 2.5 p. 100 | 48 | 11 | 8 | 0 | 0 | 45 | III |

Injections:
1 50% Freund adjuvant
2 MNIC allergen
3 mixture 1/1 adjuvant + allergen.

We claim:

1. A method of treatment of seborrhea comprising administering an anhydrous or hydrated form of zinc cysteate salt of the formula:

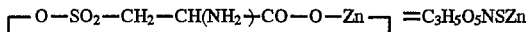

to a human being, in an amount effective to treat said seborrhea, wherein said administering of the zinc cysteate is topical.

2. The method of treatment according to claim 1, wherein the hydrated form consists of two mole equivalents of water in addition to the zinc cysteate for each mole equivalent of zinc cysteate in the composition applied.

3. A method of treatment of seborrhea comprising administering an anhydrous or hydrated form of zinc cysteate salt of the formula:

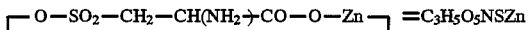

to an animal, in an amount effective to treat said seborrhea, wherein said administering of the zinc cysteate is topical.

4. The method of treatment according to claim 1, wherein said administering of the zinc cysteate is topical in a concentration of from 1 to 5%.

5. The method of treatment according to claim 3, wherein the hydrated form consists of two mole equivalents of water in addition to the zinc cysteate for each mole equivalent of zinc cysteate in the composition applied.

* * * * *